United States Patent [19]

Ethington

[11] 4,018,223
[45] Apr. 19, 1977

[54] DOSAGE CONTROL DEVICE
[75] Inventor: Gayle M. Ethington, Postville, Iowa
[73] Assignee: Andros Incorporated, Berkeley, Calif.
[22] Filed: Dec. 9, 1974
[21] Appl. No.: 530,811
[52] U.S. Cl. .......................................... 128/218 C
[51] Int. Cl.² ................................. A61M 5/00
[58] Field of Search ........................ 128/215–216, 128/218 R, 218 PA, 218 C, 234, 272; 33/1 V, 107 R, 168 R, 168 B, 174 G, 174 H; 116/121–123, DIG. 17; 137/551, 553; 141/2, 27, 94–95, 365, 375, 370, 391; 221/2–4; 222/23, 29, 31, 41, 43–45, 49, 50; 73/3, 149

[56] References Cited

UNITED STATES PATENTS

| 708,355 | 9/1902 | Hartley | 33/107 R |
|---|---|---|---|
| 3,325,061 | 6/1967 | Ellsworth | 128/218 C |
| 3,598,120 | 8/1971 | Mass | 128/218 C |
| 3,610,241 | 10/1971 | LeMarie | 128/218 C |
| 3,770,026 | 11/1973 | Isenberg | 128/218 C |
| 3,840,011 | 10/1974 | Wright | 128/215 |
| 3,844,318 | 10/1974 | Raia et al. | 128/218 C |
| 3,875,979 | 4/1975 | Hults | 128/218 C |

FOREIGN PATENTS OR APPLICATIONS

| 42,893 | 11/1933 | France | 128/215 |

Primary Examiner—John D. Yasko
Attorney, Agent, or Firm—Fitch, Even, Tabin & Luedeka

[57] ABSTRACT

A dosage control device, particularly suited for use by persons with impaired vision who from time to time may give themselves injections such as diabetic. The dosage control device is a sheet like, elongated plastic member having a transverse slot for snapping over the finger projections on the end of a standard hypodermic syringe. A scale is provided in a predetermined disposition with respect to the slot so that when the device in conjunction with the outer end of the plunger duplicates the normal scale on the syringe. In use, a doctor or other person would cut off the outward extending end of the device at the scale marking for the desired dosage, so that the diabetic could control his dosage by feel rather than sight.

6 Claims, 6 Drawing Figures

DOSAGE CONTROL DEVICE

BACKGROUND OF THE INVENTION

1. Field of the Invention

The present invention relates to the field of injection devices, and particularly to devices and methods for controlling dosages other than by visually reading a measurement scale.

2. Prior Art

Certain ailments and maladies are susceptible of control by occasional injection of a suitable drug in accordance with either a predetermined dosage and schedule or in accordance with certain physiological measurements. One such disease is diabetes, which may be maintained under reasonable control by reasonably frequent injections of insulin. These injections may be relatively easily administered, and in order to provide maximum mobility of the patient, they are often administered by the patient himself.

Impaired vision often accompanies diabetes, and therefore injection measurements which depend upon the visual reading of a scale or other indicia by the person administering his own injection is likely to result in large errors on occasion. Accordingly, it is this specific problem to which the preferred embodiment of the present invention is directed, though it is to be understood that the present invention may be used whenever non-visual dosage control for syringes is necessary or desired.

There are a number of devices which have been proposed to solve the foregoing problem. Some of these known devices are devices for mating over the cylinder of the syringe, such as that disclosed in U.S. Pat. No. 2,739,589 and U.S. Pat. No. 2,943,624. Other devices are devices to be used in conjunction with a standard syringe but not fastened thereto, such as are disclosed in U.S. Pat. Nos. 3,610,241 and 3,770,026.

A device for use in dosage control by persons with impaired vision preferably should have certain characteristics generally not found in the prior art devices. It should be small and readily carried by the user. It should be usable with standard syringes, as the cost associated with special syringes or devices forming a part of a special syringe would normally be prohibitive. It should also be readily adjusted by a doctor or other person of normal vision and yet not subject to inadvertent loss of adjustment by slippage, etc., which is not likely to be detected by persons of impaired vision.

BRIEF SUMMARY OF THE INVENTION

A dosage control device, particularly suited for use by persons with impaired vision who from time to time may give themselves injections such as diabetic. The dosage control device is sheet like, elongated plastic member having a transverse slot for snapping over the finger projections on the end of a standard hypodermic syringe. A scale is provided in a predetermined disposition with respect to the slot so that when the device is in position on the syringe, the scale on the device in conjunction with the outer end of the plunger duplicates the normal scale on the syringe. In use, a doctor or other person cuts off the outward extending end of the device at the scale marking for the desired dosage, so that the diabetic can control his dosage by feel rather than sight. The two ends of the device are preferably of substantially different geometry so that one end may be distinguished from the other end by feel to avoid inadvertent reversal of the device, particularly when cut off for control of smaller dosages. In the preferred embodiment, the outer end of the device is square, so that the geometry of the outer end does not change when cut off at the required dosage indication on the scale.

DETAILED DESCRIPTION OF THE INVENTION

Figure 1:
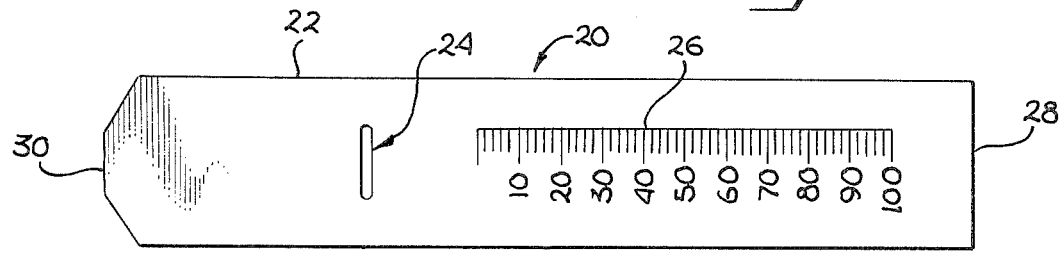
FIG. 1 is a planform view of the preferred embodiment of the present invention.

First referring to FIG. 1, a plan view of one embodiment of the present invention may be seen. The device 20 of this embodiment is characterized by an elongated plastic sheet-like member 22, which in the preferred embodiment, is a vinyl sheet having a thickness of approximately thirty thousandths of an inch. There is located adjacent one end a transverse slot 24 of predetermined and controlled dimensions. A scale 26 is provided in a predetermined spatial relationship with respect to slot 24, the scale in this embodiment ranging from 0 to 100. While the member 20 is substantially rectangular, the two ends 28 and 30 are specifically given different geometries, so as to be readily discernible by feel of the person using the device. It is particularly important that the end 30 be given some geometry substantially different than the geometry which will result at the other end when the device is cut off for use, as shall subsequently be described, and accordingly in this embodiment the end 30 is given a non square characteristic, unlike the end 28. Finally, in this embodiment there is a space provided between slot 24 and end 30 for certain printed matter, including the identification of the type and nature of the drug to be used if the scale 26 is marked off in units or a similar designation.

Figure 2:
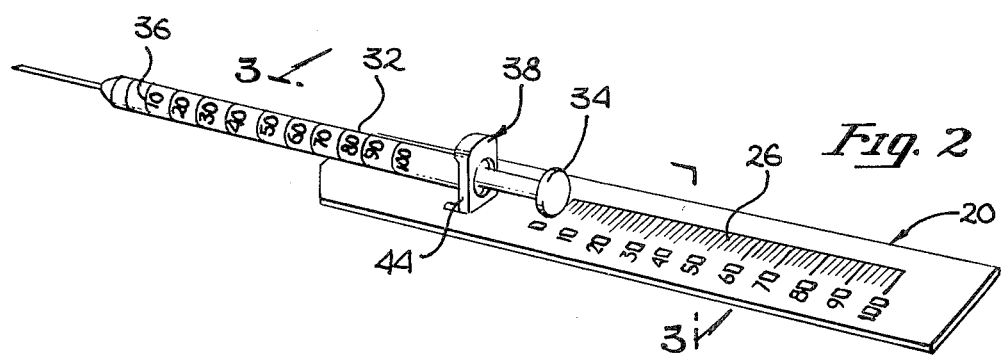
FIG. 2 is a perspective view showing the device of the present invention mounted on a standard syringe.

Now referring to FIG. 2, a perspective view of the present invention mounted on a standard plastic syringe may be seen. It will be noted that when the device of the present invention is mounted onto a standard syringe 32, the outer end 34 of the plunger is cooperatively disposed with respect to the scale 26 on device 20 of the present invention. More particularly, when the plunger is in its innermost position, e.g., the zero dosage condition, the end 34 of the plunger is also at the zero position on scale 26. Obviously, by making the scale 26 of the same length and divisions as the scale on the cylinder 36 of the plunger, the end 34 of the plunger in cooperation with the scale 26 will always provide the same reading as would be obtained with the scale on the cylinder. Accordingly, by cutting off the device 20 at the scale reading for the desired dosge, a person of impaired vision may control the dosage by using the end of the device 20 in cooperation with the end 34 of the plunger as a gauge or stop while loading the syringe with the drug to be administered.

Figure 3:
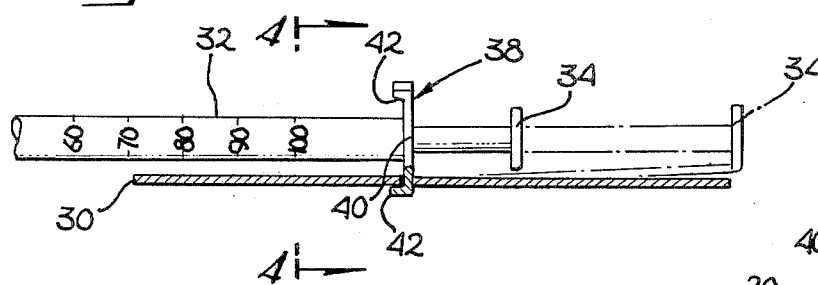
FIG. 3 is a partial cross-section taken along lines 3—3 to FIG. 2 with the device cut off at a predetermined scale setting.
Figure 4:
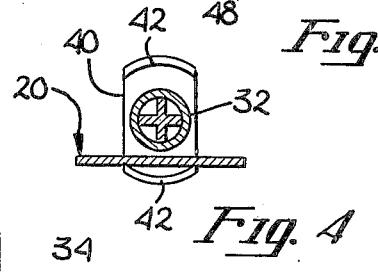
FIG. 4 is a cross-section taken along lines 4—4 of FIG. 3.

Now referring to FIG. 3, a side view of the assembly of FIG. 2 may be seen. It will be noted that the flanges of the syringe, generally indicated by the number 38, are comprised of radially outward extending members 40, with a forward extending bead or lip 42. Also, it will be noted in FIG. 2 that the sides 44 of the flanges are flattened so that the bead 42 is an arc segment, as may be seen in FIG. 4. This arc segment on conventional syringes is disposed with respect to the cylinder 32 so as to allow the disposition of the device 20 between the cylinder 32 and the lip 42, as may be seen in both FIG. 3 and FIG. 4 without requiring any curvature of the device 20 along a longitudinal axis. It is to be understood, however, that the present invention may be curved along a longitudinal axis, with the curve providing increased rigidity of the device of the present invention without resulting in cracking or fracturing when being bent about a transverse axis. In the preferred embodiment slot 24 has a width to freely but closely accommodate the widest area of the flange 38 on the cylinder 32.

Figure 5:
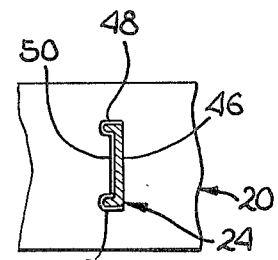
FIG. 5 is a cross-section taken along lines 5-5 of FIG. 3.

Now referring to FIG. 5, the slot 24 in an alternate embodiment of device 20 is comprised of a transverse section 46, and longitudinally extending sections 48 at the outer extremities of the transverse section so as to define a tab like member 50 for snapping over the lip 42 on the flange 38. Accordingly, though the transverse slot 46 may be made slightly wider than the thickness of the radially extending member 40 of flange 38, this embodiment of the device may be snapped into place on the syringe and will retain itself in that position by the snapping of tablike member 50 over the lip 42.

Figure 6:
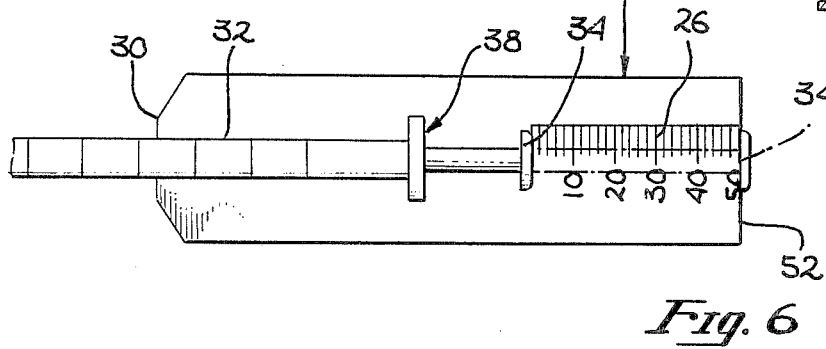
FIG. 6 is a top view of the assembly of the device of the present invention as cut off to a predetermined scale setting and mounted to a standard syringe.

New referring to FIG. 6, a top view of the assembly of the device of the present invention and a standard syringe, after the device has been cut off at a predetermined dosage level, may be seen. In particular the device as shown has been cut off to allow the control by feel of a dosage representing 50 units. It will be noted that when cut off at such a position, the linear dimension from slot 24 to end 52 is not substantially different from the linear dimension from slot 24 to end 30. However, it is very clear that the two ends are readily distinguishable by feel, and that there is substantially no opportunity for a user to mount the device onto a syringe incorrectly.

There has been described herein an extremely simple device which may be used by persons of impaired vision to control self-administered dosages of drugs by standard hypodermic syringes. The device of the present invention may be manufactured at extremely low cost, and reliably set to the desired dosage (e.g., cut off at the required length) to provide a substantially foolproof method of gauging that desired dosage. The present invention may be very easily carried by a user and may be used in conjunction with standard syringes without any modification thereof. While the preferred embodiment has been disclosed and described with respect to standard plastic syringes, it will be noted that the device may readily be changed, particularly in proportions, so as to be usable in like manner with glass syringes. In that regard, the flanges on the cylinders of glass syringes are very similar to the flanges described hereabove with respect to plastic syringes, so that the device of the present invention may be readily made to snap onto the flange of a glass syringe in the same manner as described herein.

While the preferred embodiment of the present invention has been disclosed and described herein, it will be noted that a number of modifications and additions may be made thereto. Aside from providing a curvature about a longitudinal axis as previously described, other changes may include some form of clear identification of the drug to be used therewith, such as, by way of example, some form of stamped or embossed designation which would be readily detectable by feel. This may be accomplished by embossing the drug designation into the plastic. It may also be accomplished in a very inexpensive manner by making the shape of end 30 unique with respect to each drug for which such devices are fabricated, so that the gross appearance and gross feel of the device provides an immediate identification for its intended use.

Thus, while a present invention has been disclosed and described with respect to a preferred embodiment thereof, it will be understood by those skilled in the art that various changes in form and detail may be made therein without departing from the spirit and scope of the invention.

I claim:

1. A combination for use in controlling the dosage of injections comprising: a syringe having a cylinder body with a needle on one end and at least one cylinder flange on the other end, and a plunger extending into said cylinder body and having a plunger flange on the outer end thereof; and a sheet-like plastic member of generally uniform thickness having a scale for reading in co-operation with the plunger flange and having a slot at a predetermined location with respect to said scale and snapped over said cylinder flange such that said cylinder flange protrudes through said plastic member, said plastic member being cut off at the scale reading for the desired dosage at a position less than the full travel of said plunger flange, whereby said plunger may be moved so that said plunger flange abuts the end of said member, as cut off, to control the dosage in said syringe.

2. A dosage control device for use with a standard syringe of the type which includes a body, a pair of finger flanges extending from opposite sides of the body, and a plunger having a plunger flange on the end thereof, said device comprising, an elongated sheet-like member composed of a substantially rigid but flexible and cuttable material having a substantially uniform thickness substantially less than the distance of projection of a finger flange on the syringe, said thickness being such as to be easily cut by manual means, said member having transverse slot means therein having a configuration for mating with that of one of the finger flanges on the syringe so that the flange projects beyond said member, said slot means being located with respect to the end of said member such that said member extends alongside the plunger of the syringe close enough thereto to engage the plunger side of the plunger flange when the plunger is sufficiently withdrawn and the member is cut off, said slot means being located with respect to the ends of said member such that when said slot means mates with a finger flange a portion of said member extends along the body of the syringe parallel with the axis thereof a distance sufficient to be held manually against the barrel of the syringe but less than the length of the syringe barrel, whereby said member may be cut off at the desired length at the portion thereof extending alongside the syringe plunger to provide a mechanical gauge with respect to the plunger flange on the plunger of the syringe.

3. A dosage control device according to claim 2 wherein said slot means are of a configuration for snapping over one of the finger flanges.

4. A dosage control device according to claim 2 wherein at least one end of said member is of a non-square configuration so that when the other end thereof is cut off, the ends may be distinguished by feel.

5. A dosage control device according to claim 2 wherein said member has a scale of printed indicia thereon reading along its length, said scale being on the portion of said member which extends alongside the plunger of the syringe, whereby said member may be cut off at a desired scale reading.

6. A method of controlling the dosage on a syringe comprising the steps of:
 a. providing a member having a slot therein for snapping over the flange on a syringe and having a scale thereon for reading in cooperation with the flange on the end of the plunger;
 b. cutting said member off at the scale reading for the desired dosage;
 c. snapping said member onto one of the flanges on the syringe and filling said syringe beyond the desired dosage; and
 d. pushing the plunger of the syringe in until the flange on the plunger abuts the end of the member as cut off.

* * * * *